United States Patent [19]

Krüger et al.

[11] Patent Number: 4,474,596
[45] Date of Patent: Oct. 2, 1984

[54] XYLITE DERIVATIVES, METHODS FOR THEIR PRODUCTION AS WELL AS COMPOSITIONS CONTAINING THEM HAVING GROWTH REGULATORY ACTIVITY FOR PLANTS

[75] Inventors: Hans-Rudolf Krüger; Reinhold Puttner; Hansjörg Krähmer; Ernst A. Pieroh, all of Essen, Fed. Rep. of Germany

[73] Assignee: Schering Aktiengesellschaft, Berlin and Bergkamen, Fed. Rep. of Germany

[21] Appl. No.: 380,003

[22] Filed: May 19, 1982

[30] Foreign Application Priority Data
May 22, 1981 [DE] Fed. Rep. of Germany ....... 3121156

[51] Int. Cl.³ .................... A01N 43/00; C07D 317/00
[52] U.S. Cl. ......................................... 71/88; 549/448
[58] Field of Search ........................... 549/448; 71/88

[56] References Cited
U.S. PATENT DOCUMENTS
3,331,678  7/1967  Chappelow, Jr. et al. ......... 549/448

FOREIGN PATENT DOCUMENTS
2100256  12/1982  United Kingdom ................ 549/448

Primary Examiner—Ethel G. Love
Attorney, Agent, or Firm—Michael J. Striker

[57] ABSTRACT

The invention concerns new xylite derivatives, methods for the production of these compounds as well as compositions containing them having growth regulatory activity for plants.

85 Claims, No Drawings

XYLITE DERIVATIVES, METHODS FOR THEIR PRODUCTION AS WELL AS COMPOSITIONS CONTAINING THEM HAVING GROWTH REGULATORY ACTIVITY FOR PLANTS

BACKGROUND OF THE INVENTION

Compounds with growth regulatory activity are already known and to some extent have even already been introduced in practice.

One of these products known in practice, based upon triiodobenzoic acid, indeed influences the growth of plants but it does not always work satisfactorily.

Another product, based upon 2,3:4,6-di-O-isopropylidene-2-ketogulonic acid and its sodium salt, leads, on the other hand, to morphological changes with certain decorative and culture plants, but it is limited to certain plants with regard to its use.

SUMMARY OF THE INVENTION

The object of the present invention is to make available an agent, i.e. a composition, which displays a growth regulatory activity with a broad activity spectrum, with simultaneous regard for the plants, i.e. without otherwise harming them.

This object is attained according to the present invention by a composition which is characterized by a content of at least one compound of the general formula

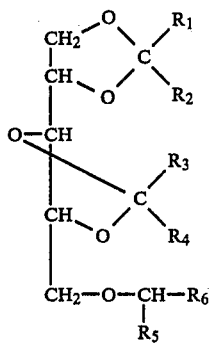

wherein $R_1$, $R_2$, $R_3$ and $R_4$ are the same or different and are each hydrogen, $C_1$–$C_{10}$-alkyl, $C_1$–$C_{10}$-alkyl substituted in one or more places by halogen, $C_1$–$C_6$-alkoxy, phenoxy and/or halogenphenoxy, aryl-$C_1$–$C_3$-alkyl, aryl-$C_1$–$C_6$-alkyl substituted in one or more places by $C_1$–$C_6$-alkyl, halogen, $C_1$–$C_6$-alkoxy, nitro and/or trifluoromethyl, a $C_3$–$C_8$-cycloaliphatic hydrocarbon group, an aromatic hydrocarbon group or an aromatic hydrocarbon group substituted in one or more places by $C_1$–$C_6$-alkyl, halogen, $C_1$–$C_6$-alkoxy, nitro and/or trifluoromethyl, or $R_1$ and $R_2$ and/or $R_3$ and $R_4$ together with the adjoining C-atom form a $C_3$–$C_8$-cycloaliphatic hydrocarbon group, $R_5$ is hydrogen or $C_1$–$C_4$-alkyl and $R_6$ is an aromatic hydrocarbon or an aromatic hydrocarbon substituted in one or more places by $C_1$–$C_6$-alkyl, $C_1$–$C_6$-alkoxy, phenoxy, phenyl, halogen, nitro and/or trifluoromethyl.

The compounds according to the present invention occur as optical, if necessary also as geometrical, isomers. The individual isomers and their mixtures are also included in the subject matter of the present invention.

The compounds according to the present invention are excellently suitable for regulating the growth of plants with different culture plants and, suprisingly, exceed in their activity spectrum as well as in their compatibility the previously mentioned products known in practice for the same activity tendencies.

Since the compounds according to the present invention bring about not only qualitative and quantitative changes in plants, but also changes in the metabolism of the plants, they are classified in the category of plant growth regulators, which are distinguished by the following possibilities of use:

Restraint of the vegetative growth with woody and herb plants, for example along road edges or in railway yards, among others, so as to eliminate too abundant a growth. Restraint of growth with cereals, e.g. corn, grain, for the purpose of eliminating depositing or breakage upon bending tendencies, with cotton, for increasing the yields.

Influencing the branching of vegetative and generative organs with decorative or culture plants for the purpose of multiplying and/or accelerating the onset of blossoming, or, with tobacco and tomato, to restrain lateral shoots.

Improving the quality of fruit, for example, an increase in the sugar content with sugar cane, with sugar beets or with fruit, and a more uniform ripening of the crop goods, which leads to higher yields.

Increasing the power of resistance against climatic influence, such as cold and drought.

Influencing the latex flow with rubber plants.

Formation of parthenogenic fruit, pollen sterility and influence of gender are likewise possibilities of use.

Control of the germination of seeds or the sloughing off of buds.

Defoliation or influencing the fruit fall to facilitate harveting.

The compounds according to the present invention are suitable, in particular, for influencing the vegetative and generative growth of legumes, such as for example soybeans.

The application amounts come to, generally, from about 0.005 to 5 kg active substance per hectare, indeed according to purpose of use, but the compounds according to the present invention can, however, if necessary, also be used in higher application amounts.

The time of application should be adjusted to the purpose of use and the climatic conditions.

Of the compounds according to the present invention, which particularly distinguish through the described effects, are those for which in the above-given general formula I, $R_1$, $R_2$, $R_3$ and $R_4$ are the same or different and are each hydrogen, methyl, ethyl, propyl, isopropyl, n-butyl, sec.-butyl, tert.-butyl, 2,2-dimethyl-1-propyl, n-pentyl, n-heptyl, n-octyl, n-decyl, chloromethyl, bromomethyl, fluoromethyl, dichloromethyl, trifluoromethyl, trichloromethyl, methyl, methoxymethyl, ethoxymethyl, phenoxymethyl, 4-chlorophenoxymethyl, chloroethyl, bromoethyl, 2-ethoxyethyl, 2-phenoxethyl, cyclopropyl, cyclopentyl, cyclohexyl, benzyl, 2-phenylethyl, phenyl, 2-chlorophenyl, 3-chlorophenyl, 4-chlorophenyl, 3,4-dichlorophenyl, 4-methoxyphenyl, 4-nitrophenyl or 2,4-dichlorophenyl, $R_5$ is hydrogen or methyl and $R_6$ is phenyl, 2-chlorophenyl, 3-chlorophenyl, 4-chlorophenyl, 2,6-dichlorophenyl, 2,4-dichlorophenyl, 3,4-dichlorophenyl, 2,4,6-trichlorophenyl, 4-bromophenyl, 2,4-dibromophenyl, 2,6-dibromophenyl, 2,4,6-tribromophenyl, 2-fluorophenyl, 3-fluorophenyl, 4-fluorophenyl, 2,4-difluorophenyl, 2-methylphenyl, 3-methylphenyl, 4-methylphenyl, 3,4-dimethylphenyl, 2-methoxyphenyl, 3-methoxyphenyl, 4-methoxyphenyl, 3,4-dioxymethylenephenyl, 2-phenoxyphenyl, 3-phenoxyphenyl, 2-nitrophenyl, 3-nitrophenyl or 4-nitrophenyl.

As compounds with more prominent activity there should be mentioned in particular 5-O-(2,6-dichlorobenzyl)-1,2:3,4-bis-O-isopropylidene-xylite, 5-O-(2,6-dichlorobenzyl)-1,2:3,4-bis-O-(ethylmethyl-methylene)-xylite and 5-O-(2,6-dichlorobenzyl)-1,2:3,4-bis-O-(methyl-propyl-methylene)-xylite The compounds according to the present invention can be used either alone, in mixture with one another, or with other effective substances. If necessary, defoliating, plant protection or pest control agents can be added, according to the desired purpose.

To the extent that a broadening of the activity spectrum is intended, also other biocides can be added. By way of example, suitable as herbicidally effective mixture partners are effective substances from the group of triazines, aminotriazoles, anilides, diazines, uracils, aliphatic carboxylic acids and halogen-carboxylic acids, substituted benzoic acids and arylcarboxylic acid, hydrazides, amides, nitriles, esters of such carboxylic acids, carbamidic acid- and thiocarbamidic acid-esters, ureas, 2,3,6-trichlorobenzyloxypropanol, thiocyanogen-containing agents and other additives.

Under "other additives" are also to be understood, for example, non-phytotoxic additives, which can provide with herbicides a synergistic increase in activity, such as, among others, wetting agents, emulsifiers, solvents and oily additives.

Expediently, the active substances according to the present invention or their mixtures are used in the form of preparations, such as powders, dusting agents, granulates, solutions, emulsions or suspensions, with the addition of liquid and/or solid carrier materials, diluting agents and, if necessary, wetting, adhesive, emulsifying and/or dispersing adjuvants.

Suitable liquid carriers include, for example, water, aliphatic and aromatic hydrocarbons, such as benzene, toluene, xylene, cyclohexanone, isopherone, dimethylsulfoxide, dimethylformamide, and, further, mineral oil fractions.

Mineral earths, for example, tonsil, silica gel, talc, kaolin, attaclay, limestone, silicic acid, and vegetable products, for example, meal flour, are suitable solid carriers.

As surface-active materials, mention should be made, for example, of calcium lignin sulfonate, polyoxyethylene-alkylphenolether, naphthalene sulfonic acids and their salts, phenol sulfonic acids and their salts, formaldehyde condensate, fatty alcohol sulfates, as well as substituted benzene sulfonic acids and their salts.

The application of the composition can follow in customary manner, for example with water as carrier in spray/soak amounts of about 100 to 1000 liter/ha. Use of the active substances according to the present invention in the so-called low-volume- and ultra-low-volume techniques is likewise possible, as is their application in the form of so-called microgranulates.

For production of the preparations, the following components are given by way of example:

A. Spray Powder (a)
40% by weight active substance
25% by weight clay minerals
20% by weight wesseling
10% by weight cell pitch
5% by weight surface-active material based upon a mixture of calcium salt of lignin sulfonic acid with alkylphenolpolyglycolether.

(b)
25% by weight active substance
60% by weight kaolin
10% by weight wesseling
5% by weight surface-active material based upon the sodium salt of N-methyl-N-oleyl-taurine and the calcium salt of lignin sulfonic acid (c)
10% by weight active substance
60% by weight clay minerals
15% by weight wesseling
100% by weight cell pitch
5% by weight surface-active material based upon the sodium salt of N-methyl-N-oleyl-taurine and the calcium salt of lignin sulfonic acid (B) Paste
45% by weight active substance
5% by weight sodium aluminum silicate
15% by weight cetylpolyglycolether with 8 mol ethylene oxide
2% by weight spindle oil
10% by weight polyethyleneglycol
23 parts water C. Emulsion Concentrate
25% by weight active substance
15% by weight cyclohexanone
55% by weight xylene
5% by weight mixture of nonylphenylpolyoxyethylene or calcium dodecylbenzene sulfonate The new compounds according to the present invention can be produced, for example, by reacting (A) compounds of the general formula

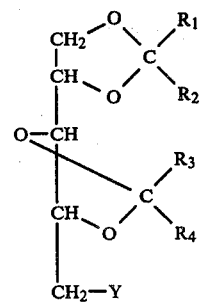
II with compounds of the general formula

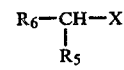
III in the presence of acid-binding agents, or (B) compounds of the general formula

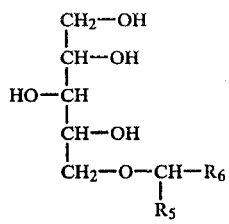  IV (a) with compounds of the general formula

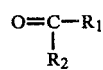  V and

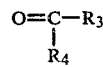  VI in the presence of acid catalysts as well as water-eliminating agents, or
(b) with compounds of the general formula

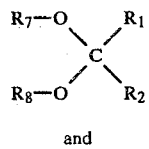  VII and

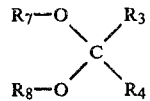  VIII in the presence of acid catalysts, wherein $R_1$, $R_2$, $R_3$, $R_4$, $R_5$ and $R_6$ have the above-stated meaning, $R_7$ and $R_8$ are the same or different and are each $C_1$–$C_4$-alkyl, and X and Y are different and are each a halogen atom or the group OZ, in which Z is a hydrogen atom or an equivalent of an alkali- or earth-alkali metal, preferably a sodium, potassium or lithium atom.

To the extent that Z represents a hydrogen atom, the reaction is performed in the presence of a base, expediently an alkali metal hydroxide, alkali metal alcoholate, alkali metal hydride or alkali metal carbonate, preferably a sodium compound.

A preferred embodiment of the method alternative A is the reaction of a compound of the general formula II, wherein Y represents a hydroxyl group, with compounds of the general formula III, whereby X represents a halogen atom, preferably a chlorine or bromine atom, in the presence of a base, for example sodium hydride or sodium hydroxide.

The conversion of the reaction partners follows at temperatures between about 0° and 150° C., generally though between room temperature and reflux temperature of the reaction mixture. The compounds of general formulas II and III can be produced by means of known methods.

For synthesis of the compounds according to the present invention, the reactants are used in about equivalent amounts. Suitable reaction media are solvents inert with respect to the reactants. The choice of solvent or suspending agent is to be guided by the respective benzyl halogenide, the acid acceptors used, and the metal compounds.

As solvent or suspending agent there may be mentioned, by way of example, ethers, such as diethylether, diisopropylether, tetrahydrofuran and dioxane, aliphatic and aromatic hydrocarbons, such as petroleum ethers, cyclohexane, hexane, heptane, benzene, toluene, xylene; carboxylic acid nitriles, such as acetonitrile, and carboxylic acid amides, such as dimethylformamide.

The reactants can though, as such, themselves possess solvent function.

For binding of the respective hydrogen halide acids, one uses tertiary amines, for example triethylamine or N,N-dimethylaniline and pyridine bases or, preferably, inorganic bases suitable for this purpose, such as oxides, hydroxides, hydrides, carbonates and alcoholates of alkali- and earth alkali-metals.

The etherification of the xylite compounds of general formula II with benzylhalogenides of the general formula III, whereby Y represents a hydroxyl group and X a halogen atom, can also be driven phase-transfer catalyzed, in known manner. These methods allow for production of the compounds according to the present invention in more simple manner, and in higher yields, using inexpensive materials.

For this purpose according to the present invention, a benzylhalogenide of the formula

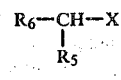  III is reacted in a two-phase system, composed of a xylite compound of formula II, if necessary diluted with an inert solvent, and an alkali hydroxide, solid or as aqueous solution, in the presence of a catalyst. Of the hydroxides, sodium hydroxide, preferably as 50% aqueous solution, is preferred.

"Onium" compounds such as quaternary ammonium, phosphonium and arsonium compounds, as well as sulfonium compounds, are suitable as catalysts.

Likewise suitable are polyglycolethers, particularly cyclicals, such as e.g. 18-crown-6, and tertiary amines, such as for example tributylamine. Preferred compounds are quaternary ammonium compounds, such as, for example, benzyltriethylammonium chloride and tetrabutylammoniumbromide.

The ratio amounts of the reactants can vary within broad limits. Preferably, the reactions are performed with 1-10-times excess of benzyl halogenide and 1-10-times excess of hydroxide. About 0.02 equivalents of catalyst are sufficient.

The reaction takes place at temperatures between about 20° and 100° C., generally however between 20° and 60° C. The duration of the reaction amounts to between about 1 and 72 hours. During the entire reaction period, good intermixing is necessary.

The above given process variants apply also for the case when compounds of the general formula II, with Y representing a halogen atom, are reacted with compounds of the general formula III, with X representing a hydroxyl group.

For synthesis of the compounds according to the present invention according to the process alternative B, the reaction partners are used in about equimolar amounts, whereby indeed the carbonyl components V and VI respectively the acetal or ketal compounds VII and VIII also can be used in excess without disadvantage, quasi as solvents. The reaction proceeds in the presence of water-eliminating agent as well as acid catalyst, such as, for example, copper sulfate, zinc chloride, ammonium chloride, sulfuric acid, p-toluenesulfonic acid, boron trifluoride-diethylether-complex, hydrogen chloride and phosphorus pentoxide. Suitable reaction media are solvents inert with respect to the reactants. Examples of the same include halogenated hydrocarbons, such as methylene chloride, chloroform and carbon tetrafluoride, aliphatic and aromatic hydrocarbons, such as pentane, hexane, heptane, cyclohexane, benzene, toluene and xylene, and the reacting ketones and aldehydes as well as ketals and acetals themselves.

The reaction takes place at temperatures between about 0° and 100° C., generally though between room temperature and reflux temperature of the respective reaction mixture. The duration of reaction is between 1 and 72 hours.

The compounds according to the present invention produced by means of the above discussed processes can be isolated from the reaction mixture according to customary techniques, for example by distilling off of the employed solvent at normal or decreased pressure, through precipitation with water, or by extraction. A higher degree of purity can be obtained as a rule by column-type chromatographic purification, or fractional distillation under decreased pressure.

The compounds according to the present invention represent as a rule liquids which are nearly colorless and odorless, which are difficultly soluble in water, of limited solubility in aliphatic hydrocarbons such as petroleum ether, hexane, pentane, and cyclohexane, well soluble in halogenated hydrocarbons such as chloroform, methylene chloride and carbon tetrachloride, aromatic hydrocarbons such as benzene, toluene and xylene, ethers such as diethylether, tetrahydrofuran and dioxane, carboxylic acid nitriles, such as acetonitrile, ketones, such as acetone, alcohols, such as methanol and ethanol, carboxylic acid amides, such as dimethylformamide, and sulfoxides, such as dimethylsulfoxide.

As already mentioned, the compounds according to the present invention occur as optical, if necessary also as geometric isomers. The particular isomers and their mixtures are also part of the subject matter of the present invention.

The novel features which are considered characteristic for the invention are set forth in particular in the appended claims. The invention itself, however, both as to its composition and its method of use, together with additional objects and advantages thereof, will be best understood from the following description of specific embodiments.

EXAMPLE 1

5-O-(2,4-dichlorobenzyl)-1,2:3,4-bis-O-isopropylidene-xylite 116.13 g (0.5 mol) 1,2:3,4-bix-O-isoprylidene-xylite are provided together with 97.74 g (0.5 mol) 2,4-dichlorobenzylchloride and 4.5 g (0.019 mol) benzyl-triethylammonium chloride. Under extremely intensive stirring, a solution of 100 g sodium hydroxide (2.5 mol) in 125 ml water is dripped into the reaction mixture, whereby the temperature slowly rises to about 50° C., and, in the course of about 1 hour, drops again to room temperature. Subsequently, for termination of the reaction, after-stirring is performed for yet a further hour at room temperature. The reaction mixture is then diluted with 500 ml ice water, and extracted three times, each with 150 ml ethyl acetate. The organic phase is washed twice, with 300 ml water each time, dried across magnesium sulfate, filtered, and evaporated in a vacuum at 40° C. The oil remaining is fractionally distilled.

Yield: 168.2 g=86.1% of theoretical amount
$Kp_{0.05\ Torr}$: 159°–161° C.; $n_D^{20}$: 1.5078
DC: flowing agent=toluene/ethyl acetate 4:1; $R_f$ value: 0.52
Analysis: Calculated: C 55.25%; H 6.18%; Cl 18.12%. Found: C 55.62%; H 6.42%; Cl 17.88%.

EXAMPLE 2

5-O-(2,6-dichlorobenzyl)-1,2:3,4-bis-O-isoprylidene-xylite

A solution of 23.2 g (0.1 mol) 1,2:3,4-bis-O-isopropylidene-xylite in 100 ml toluene is slowly dripped into a suspension of 2.88 (0.12 mol) sodium hydride in 50 ml toluene, while stirring. After the addition is accomplished, the mixture is heated for 2 hours under reflux. Subsequently, a solution of 19.54 g (0.1 mol) 2,6-dichlorobenzylchloride in 50 ml toluene is added dropwise, and the mixture is heated for 5 hours under reflux. After cooling, the mixture is washed three times, with 150 ml water each time; the organic phase is then dried across magnesium sulfate, filtered, and concentrated in a vacuum at 40° C. The oil remaining is distilled in a vacuum.

Yield: 35.8 g=91.5% of theory
$Kp_1\ Torr$: 190°–98° C.; $n_D^{20}$: 1.5080
DC: flowing agent=toluene/ethyl acetate 4:1; $R_f$ value: 0.50
Analysis: Calculated: C 55.25%; H 6.18%; Cl 18.12%. Found: C 55.66%; H 6.46%; Cl 18.03%.

EXAMPLE 3

5-O-(2-chlorobenzyl)-1,2:3,4-bis-O-isopropylidene-xylite

A solution of 11.64 g 9) 0.05 mol) 1,2:3,4-bis-O-isopropylidene-xylite in 30 ml dried dimethylformamide is reacted cautiously with 1.44 g (0.06 mol) sodium hydride. The reaction mixture is then after-stirred for 1 hour at 40° C. 8.1 g (0.05 mol) 2-chlorobenzylchloride are then dripped in, whereby the temperature rises to 55° C. For completion of the reaction, after-stirring is performed a further 2.5 hours at 55° C. The reaction mixturre is then diluted cautiously with 150 ml ice water and extracted three times, each with 200 ml ethyl acetate. The ethyl acetate phase, dried across magnesium sulfate and filtrated, is evaporated in a vacuum at 40° C. The oily residue is distilled in a bulbed tube (oven temperature): 160° C.; 0.1–0.05 Torr).

Yield: 15.4 g=86.4% of theoretical
$n_D^{20}$: 1.4978
DC: flowing agent=toluene/ethyl acetate 4:1; $R_f$ value: 0.50
Analysis: Calculated: C 60.57%; H 7.06%; Cl 9.94%. Found: C 60.50%; H 6.98%; Cl 9.70%.

EXAMPLE 4

5-O-(2,4-dichlorobenzyl)-1,2:3,4-bis-O-(methylmethylene)-xylite 9.32 g (0.03 mol) 5-O-(2,4-dichlorobenzyl)-xylite are suspended in a solution of 9.44 g (0.08 mol) acetaldehyde diethylacetal and 30 ml toluene, and subsequently reacted with 1 ml boron trifluoride-diethylether complex. Then, the reaction mixture is heated for 30 minutes to 80° C., and the produced alcohol is distilled off. After cooling, the reaction solution is washed with saturated potassium hydrogen carbonate solution, dried across magnesium sulfate, filtered, and evaporated in a vacuum at 40° C. The oil remaining is distilled in a bulbed tube (oven temperature: 190° C.; 0.01 Torr).

Yield: 8.89 g=81.5% of theory
$n_D^{20}$: 1.5283

DC: flowing agent=chloroform/methanol 4:1; $R_f$ value: 0.71

Analysis: Calculated: C 52.90%; H 5.55%; Cl 19.52%. Found: C 52.97%; H 5.75%; Cl 19.54%.

In analogous manner, the following compounds according to the present invention are prepared:

| Name | Physical Constant |
|---|---|
| 5-O—(4-bromobenzyl)-1,2;3,4-bis-O—isopropylidene-xylite | $n_D^{20}$: 1.5074 |
| 5-O—(3,4-dichlorobenzyl)-1,2;3,4-bis-O—isopropylidene-xylite | $n_D^{20}$: 1.5078 |
| 5-O—(4-chlorobenzyl)-1,2:3,4-bis-O—isopropylidene-xylite | $n_D^{20}$: 1.4975 |
| 5-O—(2-chlorobenzyl)-1,2:3,4-bis-O—isopropylidene-xylite | $n_D^{20}$: 1.4978 |
| 5-O—(3-chlorobenzyl)-1,2:3,4-bis-O—isopropylidene-xylite | $n_D^{20}$: 1.5050 |
| 5-O—(2-methylbenzyl)-1,2:3,4-bis-O—isopropylidene-xylite | $n_D^{20}$: 1.4904 |
| 5-O—(3-methylbenzyl)-1,2:3,4-bis-O—isopropylidene-xylite | $n_D^{20}$: 1.4878 |
| 5-O—(4-methylbenzyl)-1,2:3,4-bis-O—isopropylidene-xylite | $n_D^{20}$: 1.4875 |
| 5-O—(3,4-dimethylbenzyl)-1,2:3,4-bis-O—isopropylidente-xylite | $n_D^{20}$: 1.4920 |
| 5-O—(2-fluorobenzyl)-1,2:3,4-bis O—isopropylidene-xylite | $n_D^{20}$: 1.4805 |
| 5-O—(3-fluorobenzyl)-1,2:3,4-bis-O—isopropylidene-xylite | $n_D^{20}$: 1.4798 |
| 5-O—(4-fluorobenzyl)-1,2:3,4-bis-O—isopropylidene-xylite | $n_D^{20}$: 1.4789 |
| 5-O—(3-trifluoromethylbenzyl)-1,2:3,4-bis-O—isopropylidene-xylite | $n_D^{20}$: 1.4610 |
| 5-O—benzyl-1,2:3,4-bis-O—isopropylidene-xylite | $n_D^{20}$: 1.4890 |
| 5-O—(2,4-dichlorobenzyl)-1,2:3,4-bis-O—(diethyl-methylene)-xylite | $n_D^{20}$: 1.5070 |
| 5-O—(2,6-dichlorobenzyl)-1,2:3,4-bis-O—(ethyl-methyl-methylene)-xylite | $n_D^{20}$: 1.5078 |
| 5-O—(2,4-dichlorobenzyl)-1,2:3,4-bis-O—(ethyl-methyl-methylene)-xylite | $n_D^{20}$: 1.5060 |
| 5-O—(2-chlorobenzyl)-1,2:3,4-bis-O—(ethyl-methyl-methylene)-xylite | $n_D^{20}$: 1.4960 |
| 4-O—(2-methylbenzyl)-1,2:3,4-bis-O—(ethyl-methyl-methylene)-xylite | $n_D^{20}$: 1.4847 |
| 5-O—(2,6-dichlorobenzyl)-1,2:3,4-bis-O—(methyl-propyl-methylene)-xylite | $n_D^{20}$: 1.5036 |
| 5-O—(2,4-dichlorobenzyl)-1,2:3,4-bis-O—(methyl-propyl-methylene)-xylite | $n_D^{20}$: 1.5032 |
| 5-O—(2-methylbenzyl)-1,2:3,4-bis-O—(methyl-propyl-methylene)-xylite | $n_D^{20}$: 1.4884 |
| 5-O—(2-chlorobenzyl)-1,2:3,4-bis-O—(methyl-propyl-methylene)-xylite | $n_D^{20}$: 1.4911 |
| 5-O—(2,6-dichlorobenzyl-1,2:3,4-bis-O—(diethyl-methylene)-xylite | $n_D^{20}$: 1.5070 |
| 5-O—(2-methylbenzyl)-1,2:3,4-bis-O—(diethyl-methylene)-xylite | $n_D^{20}$: 1.4902 |
| 5-O—(2-chlorobenzyl)-1,2:3,4-bis-O—(diethyl-methylene)-xylite | $n_D^{20}$: 1.4980 |
| 5-O—(2-methylbenxyl)-1,2:3,4-bis-O—(benxyl-methyl-methylene)-xylite | $n_D^{20}$: 1.5496 |
| 5-O—(2-chlorobenzyl)-1,2:3,4-bis-O—(benzyl-methyl-methylene)-xylite | $n_D^{20}$: 1.5542 |
| 5-O—(2,4-dichlorobenzyl)-1,2:3,4-bis-O—(benzyl-methyl-methylene)-xylite | $n_D^{20}$: 1.5568 |
| 5-O—(2,6-dichlorobenzyl)-1,2:3,4-bis-O—(benzyl-methyl-methylene)-xylite | $n_D^{20}$: 1.5568 |
| 5-O—(2-methylbenzyl)-1,2:3,4-bis-O—(benzyl-methyl-methylene)-xylite | $n_D^{20}$: 1.4844 |
| 5-O—(2-chlorobenzyl)-1,2:3,4-bis-O—(1,1-tetramethylene-methylene)-xylite | $n_D^{20}$: 1.5220 |
| 5-O—(2,4-dichlorobenzyl)-1,2:3,4-bis-O—(1,1-tetramethylene-methylene)-xylite | $n_D^{20}$: 1.5282 |
| 5-O—(2-chlorobenzyl)-1,2:3,4-bis-O—(butyl-methyl-methylene)-xylite | $n_D^{20}$: 1.4898 |
| 5-O—(2,4-dichlorobenzyl)-1,2:3,4-bis-O—(butyl-methyl-methylene)-xylite | $n_D^{20}$: 1.4950 |
| 5-O—(2-methylbenzyl)-1,2:3,4-bis-O—(1,1-tetramethylene-methylene)-xylite | $n_D^{20}$: 1.5148 |
| 5-O—(2,6-dichlorobenzyl)-1,2:3,4-bis-O—(butyl-methyl-methylene)-xylite | $n_D^{20}$: 1.4946 |
| 5-O—(2,6-dichlorobenzyl)-1,2:3,4-bis-O—(1,1-tetramethylene-methylene)-xylite | $n_D^{20}$: 1.5303 |
| 5-O—(2-chlorobenzyl)-1,2:3,4-bis-O—[(2-phenylethyl)-methyl-methylene]-xylite | $n_D^{20}$: 1.5326 |
| 5-O—(2,4-dichlorobenzyl)-1,2:3,4-bis-O—[(2-phenylethyl)-methyl-methylene]-xylite | $n_D^{20}$: 1.5433 |
| 5-O—(2,4-dichlorobenzyl)-1,2:3,4-bis-O—(methyl-methylene)-xylite | $n_D^{20}$: 1.5283 |
| 5-O—(4-phenylbenzyl)-1,2:3,4-bis-O—isopropylidene-xylite | Fp.: 60° C. |
| 5-O—(4-cyanobenzyl)-1,2:3,4-bis-O—isopropylidene-xylite | Fp.: 67° C. |
| 5-O—(2,6-dichlorobenzyl)-1,2:3,4-bis-O—(2-phenylethyl)-methyl-methylene-xylite | $n_D^{20}$: 1.5526 |
| 5-O—(2-methylbenzyl)-1,2:3,4-bis-O—(2-phenylethyl)-methyl-methylene-xylite | $n_D^{20}$: 1.5427 |
| 5-O—(2,6-dichlorobenzyl)-1,2:3,4-bis-O—(4-chlorophenyl-methylene)-xylite | Fp.: 201° C. |
| 5-O—(2-chlorobenzyl)-1,2:3,4-bis-O—(phenylmethylene)-xylite | Fp.: 155° C. |
| 5-O—(2,4-dichlorobenzyl)-1,2:3,4-bis-O—(4-chlorophenyl-methylene)-xylite | Fp.: 174–175° C. |
| 5-O—(2-methylbenzyl)-1,2:3,4-bis-O—(4-chlorophenyl-methylene)-xylite | Fp.: 174° C. |
| 5-O—(2,6-dichlorobenzyl)-1,2:3,4-bis-O—(phenyl-methylene)-xylite | Fp.: 205° C. |
| 5-O—(2,6-dichlorobenzyl)-1,2:3,4-bis-O—(methyl-methylene)-xylite | Fp.: 112° C. |
| 5-O—(2-methylbenzyl)-1,2:3,4-bis-O—(methyl-methylene)-xylite | $n_D^{20}$: 1.5174 |
| 5-O—(2-chlorobenzyl)-1,2:3,4-bis-O—(methyl-methylene)-xylite | $n_D^{20}$: 1.5281 |
| 5-O—(2,6-dichlorobenzyl)-1,2:3,4-bis-O—(chloromethyl-methylene)-xylite | $n_D^{20}$: 1.5391 |
| 5-O—(2,4-dichlorobenzyl)-1,2:3,4-bis-O—(chloromethyl-methylene)-xylite | $n_D^{20}$: 1.5358 |
| 5-O—(2-methylbenzyl)-1,2:3,4-bis-O—(chloromethyl-methylene)-xylite | $n_D^{20}$: 1.5263 |
| 5-O—(2-chlorobenzyl)-1,2:3,4-bis-O—(chloromethyl-methylene)-xylite | $n_D^{20}$: 1.5250 |
| 5-O—(2,6-dichlorobenzyl)-1,2:3,4-bis-O—(methylene)-xylite | Fp.: 102° C. |
| 5-O—(2,4-dichlorobenzyl)-1,2:3,4-bis-O—(methylene)-xylite | Fp.: 65–66° C. |
| 5-O—(2-methylbenzyl)-1,2:3,4-bis-O—(methylene)-xylite | $n_D^{20}$: 1.5267 |

-continued

| Name | Physical Constant |
|---|---|
| 5-O—(2,4-dichlorobenzyl)-1,2:3,4-bis-O—(methyl-octyl-methylene)-xylite | $n_D^{20}$: 1.4900 |
| 5-O—(2,6-dichlorobenzyl)-1,2:3,4-bis-O—(methyl-octyl-methylene)-xylite | $n_D^{20}$: 1.4921 |
| 5-O—(2-methylbenzyl)-1,2:3,4-bis-O—(methyl-octyl-methylene)-xylite | $n_D^{20}$: 1.4784 |
| 5-O—(2-chlorobenzyl)-1,2:3,4-bis-O—(methyl-octyl-methylene)-xylite | $n_D^{20}$: 1.4852 |
| 5-O—(2,4-dichlorobenzyl)-1,2:3,4-bis-O—(phenyl-methylene)-xylite | Fp.: 178° C. |
| 5-O—(2-methylbenzyl)-1,2:3,4-bis-O—(phenyl-methylene)-xylite | Fp.: 156–157° C. |
| 5-O—(2,4-dichlorobenzyl)-1,2:3,4-bis-O—[(2,6-dichlorophenyl)-methylene]-xylite | Fp.: 156° C. |
| 5-O—(2-methylbenzyl)-1,2:3,4-bis-O—[(2,6-dichlorophenyl)-methylene]-xylite | Fp.: 191–192° C. |
| 5-O—(2-chlorobenzyl)-1,2:3,4-bis-O—(2,6-dichlorophenyl)-methylene-xylite | Fp.: 207–208° C. |
| 5-O—(2,6-dichlorobenzyl)-1,2:3,4-bis-O—[(2,6-dichlorophenyl)-methylene]-xylite | Fp.: 183–184° C. |
| 5-O—(2,4,6-tribromobenzyl)-1,2:3,4-bis-O—isopropylidene-xylite | $n_D^{20}$: 1.5516 |
| 5-O—(1,-phenylethyl)-1,2:3,4-bis-O—isopropylidene-xylite | $n_D^{20}$: 1.4860 |
| 5-O—[1-(2,4-dichlorophenyl)-ethyl]-1,2:3,4-bis-O—isopropylidene-xylite | $n_D^{20}$: 1.5168 |
| 5-O—[(2,6-dichlorophenyl)-ethyl]-1,2:3,4-bis-O—isopropylidene-xylite | $n_D^{20}$: 1.5158 |
| 5-O—(2,6-dichlorobenzyl)-1,2:3,4-bis-O—(methyl-phenoxymethyl-methylene)-xylite | $n_D^{20}$: 1.5598 |
| 5-O—(2,4-dichlorobenzyl)-1,2:3,4-bis-O—(methyl-phenoxymethyl-methylene)-xylite | $n_D^{20}$: 1.5579 |

The starting compounds for production of the compounds according to the present invention are known, or can be produced by known processes, such as described in J. Chem. Soc. (London) 1965, 3382.

The following examples illustrate the production of the starting compounds:

A. COMPOUNDS OF GENERAL FORMULA II a. 1,2:3,4-bis-O-(ethyl-methyl-methylene)-xylite 50 g (0.328 mol) xylite was suspended at room temperature in 1 ml dry ethylmethylketone. Under good stirring, 10 ml concentrated sulfuric acid are added all at once. At room temperature, the reaction mixture is stirred for 48 hours, whereby after about 5 hours the entire xylite has gone into solution, and the reaction solution is colored red-brown. After reaction has finished, the solution is adjusted with about 50 ml 32% caustic soda, under stirring, whereby the solution is again decolorized. The aqueous phase is separated, and the organic phase dried across magnesium sulfate and evaporated in water-jet vacuum at 40° C. The residue is fractionally distilled.

Yield: 63.5 g=74.4% of theoretical amount
$Kp_{0.6\ Torr}=118°$ C.; $n_D^{20}=1.457$
DC: flowing agent=toluene/ethyl acetate 4:1; $R_f$-value=0.22
Analysis: Calculated: C 59.97%; H 9.29%; O 30.73%. Found: C 59.50%; H 9.41%; O 31.12%.

(b) 1,2:3,4-bis-O-(phenyl-methylene)-xylite 30 g (0.197 mol) xylite are suspended in 150 ml toluene, and reacted with 71.04 g (0.393 mol) benzaldehydediethylacetal. Subsequently, 150 mg p-toluene sulfonic acid hydrate are added, and the reaction mixture is heated to 80° C., whereby the xylite slowly goes into solution, and the reaction product crystallizes out. After cooling, the crystals are sucked off, after-washed with 100 ml ether, and dried until constant weight in a vacuum at 40° C.

Yield: 61.2 g=94.6% of theoretical amount
Fp.: 139° C. (colorless crystals)
DC: flowing agent=chloroform/methanol 4:1; $R_f$-value=0.59
Analysis: Calculated: C 69.49%; H 6.14%. Found: C 69.07%; H 6.43%.

In analogous manner, the following starting products are prepared:

| Name | Physical Constant |
|---|---|
| 1,2:3,4-bis-O—isopropylidene-xylite | $n_D^{20}$: 1.4530 |
| | $Kp_{0.4\ mm}$: 103–105° C. |
| | Fp.: 33° C. |
| 1,2:3,4-bis-O—(diethyl-methylene)-xylite | $n_D^{20}$: 1.466 |
| | $Kp_{0.4\ Torr}$: 120° C. |
| 1,2:3,4-bis-O—(benzyl-methyl-methylene)-xylite | $n_D^{20}$: 1.542 |
| | $Kp_{0.01\ Torr}$: 215–20° C. |
| 1,2:3,4-bis-O—(methyl-propyl-methylene)-xylite | $n_D^{20}$: 1.547 |
| | $Kp_{0.3\ Torr}$: 136° C. |
| 1,2:3,4-bis-O—(methyl-(2-phenyl-ethyl)-methylene)-xylite | $n_D^{20}$: 1.535 |
| 1,2:3,4-bis-O—(butyl-methyl-methylene)-xylite | |
| 1,2:3,4-bis-O—(1,1-tetramethylene-methylene)-xylite | $n_D^{20}$: 1.494 |
| | $Kp_{0.1\ Torr}$: 160° C. |
| 1,2:3,4-bis-O—(phenyl-methylene)-xylite | Fp.: 139° C. |
| 1,2:3,4-bis-O—(methylene)-xylite | |
| | $n_D^{20}$: 1.4816 |
| 1,2:3,4-bis-O—(chloromethyl-methylene)-xylite | $n_D^{20}$: 1.4958 |
| 1,2:3,4-bis-O—(methyl-methylene)-xylite | Fp.: 134–135° C. |
| 1,2:3,4-bis-O—(4-chlorophenyl-methylene)-xylite | Fp.: 212–213° C. |
| 1,2:3,4-bis-O—(methyl-octyl-methylene)-xylite | $n_D^{20}$: 1.4613 |

B. COMPOUNDS OF THE GENERAL FORMULA IV

5-O-(2,4-dichlorobenzyl)-xylite 10.2 g (0.026 mol) 5-O-(2,4-dichlorobenzyl)-1,2:3,4-bis-O-isopropylidene-xylite are added to 27.7 ml 1.5 n sulfuric acid at room temperature. Subsequently, after heating under good stirring 2.4 hours to 70° C., the reaction solution is cooled, and adjusted with about 4 ml 32% caustic soda to pH 8. Then it is extracted twice with 100 ml ethyl acetate each time. The organic phase is dried across magnesium sulfate, filtered, and concentrated in a vacuum. Colorless crystals are obtained, which are digested with 50 ml cold diisopropylether. Recrystallization from toluene is then performed.

Yield: 6.4 g=79.0% of theoretical amount
Fp.: 96°–98° C.
DC: flowing agent=chloroform/methanol 4:1; $R_f$-value=0.330
Analysis: Calculated: C 46.32%; H 5.18%; Cl 22.79%. Found: C 46.32%; H 5.27%; Cl 22.45%.

In analogous manner, the following starting products are produced:

| Name | Physical Constant |
|---|---|
| 5-O—(2,6-dichlorobenzyl)-xylite | Fp.: 82–83° C. |
| 5-O—(2-chlorobenzyl)-xylite | Fp.: 52–54° C. |
| 5-O—(2-methylbenzyl)-xylite | Fp.: 59–61° C. |

The following example illustrates the possibilities of use of the compounds according to the present invention.

EXAMPLE 5

Growth Modification with Cress

In the laboratory, cress seeds are treated with an aqueous emulsion of the composition according to the present invention.

The concentration of effective substance in the emulsion is 100 ppm.

A mounting slide is placed for this purpose in a 200 ml glass connection with 10 ml effective substance emulsion. Filter paper is put onto the mounting slide. When the filter paper is saturated with the solution, 10 cress seeds are uniformly distributed thereupon. The lid of a Petri disk is placed on the connection. For each substance, two glass connections are prepared, one as described, and the second using only water, as the control.

Evaluation is performed after 7 days, with the lengths of the shoots and roots of the sprouted seeds being measured.

An average is taken of the so-obtained values, in cm, and given in the following Table. There, the values are given in relation to the control, and specified in percent.

The results show that the compounds according to the present invention exert a strong influence on root and shoot growth with cress. This is evident in the promotion (>100%) or restraint (<100%) of the particular parts.

| Compound According to the Present Invention | Growth in % | |
|---|---|---|
| | Shoot | Root |
| 5-O—(4-bromobenzyl)-1,2:3,4-bis-O—isopropylidene-xylite | 75 | 138 |
| 5-O—(2,6-dichlorobenzyl)-1,2:3,4-bis-O—isopropylidene-xylite | 75 | 125 |
| 5-O—(3,4-dichlorobenzyl)-1,2:3,4-bis-O—isopropylidene-xylite | 88 | 100 |
| 5-O—(2,4-dichlorobenzyl)-1,2:3,4-bis-O—isopropylidene-xylite | 75 | 88 |
| 5-O—(4-chlorobenzyl)-1,2:3,4-bis-O—isopropylidene-xylite | 75 | 275 |
| 5-O—(2-chlorobenzyl)-1,2:3,4-bis-O—isopropylidene-xylite | 88 | 113 |
| 5-O—(3-chlorobenzyl)-1,2:3,4-bis-O—isopropylidene-xylite | 88 | 200 |
| 5-O—(2-methylbenzyl)-1,2:3,4-bis-O—isopropylidene-xylite | 100 | 225 |
| 5-O—(3-methylbenzyl)-1,2:3,4-bis-O—isopropyldene-xylite | 88 | 138 |
| 5-O—(4-methylbenzyl)-1,2:3,4-bis-O—isopropyldene-xylite | 88 | 125 |
| 5-O—(3,4-dimethylbenzyl)-1,2:3,4-bis-O—isopropylidene-xylite | 88 | 200 |
| 5-O—(2-fluorobenzyl)-1,2:3,4-bis-O—isopropylidene-xylite | 88 | 250 |
| 5-O—(3-fluorobenzyl)-1,2:3,4-bis-O—isopropylidene-xylite | 88 | 150 |
| 5-O—(4-fluorobenzyl)-1,2:3,4-bis-O—isopropylidene-xylite | 100 | 113 |
| 5-O—(3-trifluoromethylbenzyl)-1,2:3,4-di-O—isopropylidene-xylite | 71 | 114 |
| 5-O—benxyl-1,2:3,4-bis-O—(isopropylidene)-xylite | 83 | 156 |
| 5-O—(2,4-dichllorobenzyl)-1,2:3,4-bis- | 83 | 122 |
| (diethyl-methylene)-xylite | | |
| 5-O—(2-methylbenzyl)-1,2:3,4-bis-O—(ethyl-methyl-methylene)-xylite | 100 | 89 |
| 5-O—(2,4-dichlorobenzyl)-1,2:3,4-bis-O—(methyl-propyl-methylene)-xylite | 100 | 89 |
| 5-O—(2-methylbenzyl)-1,2:3,4-bis-O-(methyl-propyl-methylene)-xylite | 80 | 17 |
| 5-O—(2,6-dichlorobenzyl)-1,2:3,4-bis-O—(diethylene-methylene)-xylite | 100 | 171 |
| 5-O—(2-methylbenzyl)-1,2:3,4-bis-O—(diethyl-methylene)-xylite | 83 | 186 |
| 5-O—(2-chlorobenzyl)-1,2:3,4-bis-O—(diethyl-methylene)-xylite | 100 | 114 |
| 5-O—(2,4-dichlorobenzyl)-1,2:3,4-bis-O—(methyl-methylene)-xylite | 83 | 143 |

EXAMPLE 6

Increased Chlorophyll Content of Soy Leaves

In a greenhouse, soy plants about 1 week old are treated with an aqueous emulsion of the compounds according to the present invention. Converted, the concentration amounts to about 0.8 kg AS/500 l spray broth.

After 7 weeks' cultivation, leaf disks with a diameter of about 1.7 cm had punched out from the fifth developed leaf blade (i.e. the third feather blade). Subsequently, the chlorophyll of the disks is ethanolically extracted. The amount of chlorophyll in the extract is determined photometrically at 665 nm.

The chlorophyll a-portion, in percent, in comparison to the control, is presented in the Table for the particular treatments. An increased content is indicated by values above 100%.

| Compound According to the Present Invention | Chlorophyll Content in % relative to the control |
|---|---|
| 5-O—(2,6-dichlorobenyl)-1,2:3,4-di-O—isopropylidene-xylite | 290 |
| 5-O—(2,6-dichlorobenzyl)-1,2:3,4-bis-O—ethyl-methyl-methylene)-xylite | 262 |
| 5-O—(2,4-dichlorobenzyl)-1,2:3,4-bis-O—(ethyl-methyl-methylene)-xylite | 154 |
| 5-O—(2-chlorobenzyl)-1,2:3,4-bis-O—(ethyl-methyl-methylene)-xylite | 126 |
| 5-O—(2,6-dichlorobenzyl)-1,2:3,4-bis-O—(methyl-propyl-methylene)-xylite | 174 |

EXAMPLE 7

Influencing the Growth of Cucumber, Bushbean and Soy

Cucumbers, bushbeans and soybeans, in two different stages of development, are sprayed with an application amount of 1 kg emulsified active substance in 500 l spray broth, each spraying. The sprayings are performed 3 and 8 days after the sowing. Three weeks later, the average length of the plants, the number of internodes, and the number of buds per plant are determined.

The results are displayed in the following Table. The percent values presented there are given relative to the control.

One learns from these numbers that the named compounds lead to a growth restraint (length <100) with often almost constant number of internodes. Moreover, in the tests with bushbeans, the number of buds is increased (>100).

| Compounds According to the Present Invention | Plants | Time of Spraying (days after sowing) | Length | Number of Internodes | Buds |
|---|---|---|---|---|---|
| 5-O—(2,4-dichlorobenzyl)-1,2:3,4-bis-O—iso-propylidene-xylite | Cucumber | 3 | 83 | 93 | — |
| | | 8 | 50 | 93 | — |
| | Bushbean | 3 | 82 | 100 | 130 |
| | | 8 | 76 | 90 | 171 |
| | Soybean | 3 | 88 | 109 | — |
| | | 8 | 83 | 100 | — |
| 5-O—(2,6-dichloro-benzyl-1,2:3,4-bis-O—isopropylidene-xylite | Cucumber | 3 | 133 | 111 | — |
| | | 8 | 60 | 80 | — |
| | Bushbean | 3 | 52 | 92 | 110 |
| | | 8 | 65 | 117 | 257 |
| | Soybean | 3 | 82 | 88 | — |
| | | 8 | 76 | 78 | — |

EXAMPLE 8

Growth Regulation with Soybean Plants-Branching

Seeds of soy are steeped with the powdery formulated compounds according to the present invention using an application amount of 25 and 250 mg active substance per 100 kg seed. The steeped seeds are placed in culture dishes with 500 ml earth, 7 per dish. After 5 weeks' cultivation in a greenhouse, the growth and morphological particulars of the plants are appraised.

The results are set down in the following Table. In connection therewith, the average value per plant is given.

It is evident, that with the application of compounds according to the present invention, branching of the plants is strongly promoted. This is manifested, among other means, in the lengths of the branchings from the cotyledon shoulders. Therewith also the number of internodes per plant can be impaired.

EXAMPLE 9

Growth Regulatory Effect with Soy-Accelerated Development of the Generative Phase Soybeans are put into culture dishes under greenhouse conditions. Two weeks after the sowing, the emulsified active substance is sprayed onto the plants in different application amounts. Seven weeks after the sowing, the length of the plants, the number of blooms and buds, as well as the number of pods and pod starts (bulges) are determined.

The results of these tests are set forth in the following Table as percentages relative to the control.

The results show that, in addition to the already described restraints of growth (length <100) and promotion of branching (>100), both of the compounds according to the present invention used influenced the generative phase. This is substantiated by the increased number of pods and pod starts.

The plants bloom earlier and are, at the point in time of the evaluation, in a further stage of development than with the control. The comparison substance is phyto-

| Compounds According to the Present Invention | Dose mg/100 kg | Length of Branching from the Cotyledon Shoulder, in cm | Length of the Other Branch, in cm | Length of the Plant, in cm | Number of Internodes |
|---|---|---|---|---|---|
| 5-O—(2,4-dichlorobenzyl)-1,2:3,4-bis-O—iso-propylidene-xylite | 25 | 1.8 | 1.4 | 28 | 4.8 |
| | 250 | 2.0 | 1.7 | 26 | 5 |
| 5-O—(2,6-dichlorobenzyl)-1,2:3,4-bis-O—iso-propylidene-xylite | 25 | 5.1 | 2.4 | 23 | 3.7 |
| | 250 | 2.1 | 2.0 | 16 | 1.7 |
| Control | — | | 1.6 | 34 | 6.2 | toxic and provides substantially less of a growth regulating effect.

| Compound According to the Present Invention | Dose (g active agent/ha) | Length | Blooms and Buds | Pod Starts | Pods (>2 cm) | Branching |
|---|---|---|---|---|---|---|
| 5-O—(2,4-dichlorobenzyl)-1,2:3,4-bis-O—isopropylidene-xylite | 1000 | 100 | 115 | 134 | 143 | 127 |
| 5-O—(2,6-dichlorobenzyl)-1,2:3,4-bis-O—isopropylidene-xylite | 100 | 70 | 36 | 159 | 150 | 180 |
| Comparison Agent | | | | | | |
| triiodobenzoic acid | 70 | 58 | 111 | 62 | 0 | 190 |
| | 7 | 42 | 93 | 21 | 0 | 136 |

EXAMPLE 10

Growth Regulatory Effect with Soy

Soybeans are cultivated under greenhouse conditions. The spray treatment follows with different emulsified effective substances, both before and after germination. Six weeks after the sowing, the number of branchings per plant is registered.

The results are given in the following Table.

The compounds according to the present invention are better than the comparison agent with regard to growth regulatory activity.

| | | Branchings per Plant | |
|---|---|---|---|
| Compound According to the Present Invention | Dose (kg effective substance/ ha) | Application Before Germination | Application After Germination |
| 5-O—(2,6-dichlorobenzyl)-1,2:3,4-bis-O—isopropylidene-xylite | 1 | 4 | 0.5 |
| Comparison Agent | | | |
| 2,3:4,6-di-O—isopropylidene-2-ketogulonic acid/sodium salt | 2.5 | 0 | 0.2 |
| | 5 | 0 | 0.2 |
| Control | — | 0 | 0 |

EXAMPLE 11

Soybeans are treated with an application amount of 0.8 kg AS/ha, after germination.

Three weeks after the spraying, the deformation of the leaves, the leaf position and the branchings are registered, and classified, each according to the degree of the visible symptoms using the following scheme: 0=no effect, ..., 4=very strongly pronounced morphogenetic effect.

At the same time, leaf disks had punched out from the third feather blade. The chlorophyll is extracted from the leaf disks, and the chlorophyll a-content determined photometrically.

The classification values for the morphological effects and the increase in chlorophyll content are given in the following Table, in comparison to the control.

The results show that with the spray concentration employed, the growth regulatory effect of the compounds according to the present invention is substantially more strongly pronounced than with the comparison substance.

TABLE

Morphological Effect and Increase in Chlorophyll Content with Soybeans

| Name | Morphological Effect/ Classification | Increase in Chlorophyll a-Content, in % |
|---|---|---|
| 5-O—(2,6-dichlorobenzyl)-1,2:3,4-bis-O—(benzyl-methyl-methylene)xylite | 2 | 25 |
| 5-O—(2,6-dichlorobenzyl)-1,2:3,4-bis-O—(butyl-methyl-methylene)-xytile | 3 | 33 |
| 5-O—(2,6-dichlorobenzyl)-1,2:3,4-bis-O—(1,1-tetramethylene-methylene)-xylite | 4 | 31 |
| 5-O—(2,4-dichlorobenzyl)-1,2:3,4-bis-O—[(2-phenyl-ethyl)-methyl-methylene]-xylite | 0 | 12 |
| 5-O—(2,4-dichlorobenzyl)-1,2:3,4-bis-O—(methyl-methylene)-xylite | 0 | 17 |
| 5-O—(2,6-dichlorobenzyl)-1,2:3,4-bis-O—(2-phenyl-ethyl)-methyl-methylene-xylite | 2 | 14 |
| 5-O—(2,6-dichlorobenzyl)-1,2:3,4-bis-O—(4-chloro-phenyl-methylene)-xylite | 3 | 19 |
| 5-O—(2,4-dichlorobenzyl)-1,2:3,4-bis-O—(4-chloro-phenyl-methylene)-xylite | 0 | 16 |
| 5-O—(2,6-dichlorobenzyl)-1,2:3,4-bis-O—(methyl-methylene)-xylite | 1 | 5 |
| 5-O—(2,6-dichlorobenzyl)-1,2:3,4-bis-O—(chloro-methyl-methylene)-xylite | 1 | 12 |
| 5-O—(2,6-dichlorobenzyl)-1,2:3,4-bis-O—(methylene)-xylite | 4 | 42 |
| 5-O—(2,4-dichlorobenzyl)-1,2:3,4-bis-O—(methyl-Octyl-methylene)-xylite | 0 | 25 |
| 5-O—(2,6-dichlorobenzyl)-1,2:3,4-bis-O—(methyl-Octyl-methylene)-xylite | 3 | 15 |
| 5-O—(2,4-dichlorobenzyl)-1,2:3,4-bis-O—[(2,6-dicholorophenyl)-methylene]-xylite | 0 | 8 |
| 5-O—(2-chlorobenzyl)-1,2:3,4-bis-O—(2,6-dicholorophenyl)-methylene-xylite | 0 | 17 |
| 5-O—(2,6-dichlorobenzyl)-1,2:3,4-bis-O—(methyl-phenoxymethyl-methylene)-xylite | 1 | 20 |
| Comparison Agent | | |
| 2,3:4,6-di-O—isopropylidene-2-ketogulonic acid/sodium salt | 0 | 6 |

It will be understood that each of the elements described above, or two or more together, may also find a useful application in other types of growth regulation different from the types described above.

While the invention has been illustrated and described as embodied in xylite derivatives, methods for the production of these compounds, as well as compositions containing them with growth regulatory activity for plants, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

We claim:

1. Xylite derivatives of the general formula

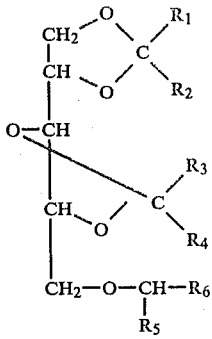

wherein $R_1$, $R_2$, $R_3$ and $R_4$ are the same or different and are each hydrogen, a $C_1$–$C_{10}$-alkyl, $C_1$–$C_{10}$-alkyl substituted in one or more places by halogen, $C_1$–$C_6$-alkoxy, phenoxy and/or halogen-phenoxy, aryl-$C_1$–$C_3$-alkyl, aryl-$C_1$–$C_3$-alkyl substituted in one or more places by $C_1$–$C_6$-alkyl, halogen, $C_1$–$C_6$-alkoxy, nitro and/or trifluoromethyl, $C_3$–$C_8$-cycloaliphatic hydrocarbon group, aromatic hydrocarbon group, or an aromatic hydrocarbon group substituted in one or more places by $C_1$–$C_6$-alkyl, halogen, $C_1$–$C_6$-alkoxy, nitro and/or trifluoromethyl or $R_1$ and $R_2$ and/or $R_3$ and $R_4$ together with the adjoining C-atom are a $C_3$–$C_8$-cycloaliphatic hydrocarbon group, $R_5$ is hydrogen or a $C_1$–$C_4$-alkyl and $R_6$ is an aromatic hydrocarbon group or an aromatic hydrocarbon group substituted in one or more places by $C_1$–$C_6$-alkyl, $C_1$–$C_6$-alkoxy, phenoxy, phenyl, halogen, nitro and/or trifluoromethyl.

2. Benzylether derivatives of the xylites according to claim 1, wherein $R_1$, $R_2$, $R_3$ and $R_4$ are the same or different and are each methyl, ethyl, propyl, isopropyl, n-butyl, sec.-butyl, tert.-butyl, 2,2-dimethyl-1-propyl, n-pentyl, n-heptyl, n-octyl, n-decyl, chloromethyl, bromomethyl, fluoromethyl, dichloromethyl, trifluoromethyl, trichloromethyl, methoxymethyl, ethoxymethyl, phenoxymethyl, 4-chlorophenoxymethyl, chloroethyl, bromoethyl, 2-ethoxyethyl, 2-phenoxyethyl, cyclopropyl, cyclopentyl, cyclohexyl, benzyl, 2-phenyl-ethyl, phenyl, 2-chlorophenyl, 3-chlorophenyl, 4-chlorophenyl, 3,4-dichlorophenyl, 4-methoxyphenyl, 4-nitrophenyl, or 2,4-dichlorophenyl, $R_5$ is hydrogen or methyl and $R_6$ is phenyl, 2-chlorophenyl, 3-chlorophenyl, 4-chlorophenyl, 2,6-dichlorophenyl, 2,4-dichlorophenyl, 3,4-dichlorophenyl, 2,4,6-trichlorophenyl, 4-bromophenyl, 2,4-dibromophenyl, 2,6-dibromophenyl, 2,4,6-tribromophenyl, 2-fluorophenyl, 3-fluorophenyl, 4-fluorophenyl, 2,4-difluorophenyl, 2-methylphenyl, 3-methylphenyl, 4-methylphenyl, 3,4-dimethylphenyl, 2-methoxyphenyl, 3-methoxyphenyl, 4-methoxyphenyl, 3,4-dioxymethylenephenyl, 2-phenoxyphenyl, 3-phenoxyphenyl, 2-nitrophenyl, 3-nitrophenyl or 4-nitrophenyl.

3. Compound according to claim 1 which is 5-O-(2,4-dichlorobenzyl)-1,2:3,4-bis-O-isopropylidene-xylite.

4. Compound according to claim 1 which is 5-O-(2,6-dichlorobenzyl)-1,2:3,4-bis-O-isopropylidene-xylite.

5. Compound according to claim 1 which is 5-O-(2-chlorobenzyl)-1,2:3,4-bis-O-isopropylidene-xylite.

6. Compound according to claim 1 which is 5-O-(2,4-dichlorobenzyl)-1,2:3,4-bis-O-(methyl-methylene)-xylite.

7. Compound according to claim 1 which is 5-O-(4-bromobenzyl)-1,2:3,4-bis-O-isopropylidene-xylite.

8. Compound according to claim 1 which is 5-O-(3,4-dichlorobenzyl)-1,2:3,4-bis-O-isopropylidene-xylite.

9. Compound according to claim 1 which is 5-O-(4-chlorobenzyl)-1,2:3,4-bis-O-isopropylidene-xylite.

10. Compound according to claim 1 which is 5-O-(2-chlorobenzyl)-1,2:3,4-bis-O-isopropylidene-xylite.

11. Compound according to claim 1 which is 5-O-(3-chlorobenzyl)-1,2:3,4-bis-O-isopropylidene-xylite.

12. Compound according to claim 1 which is 5-O-(2-methylbenzyl)-1,2:3,4-bis-O-isopropylidene-xylite.

13. Compound according to claim 1 which is 5-O-(3-methylbenzyl)-1,2:3,4-bis-O-isopropylidene-xylite.

14. Compound according to claim 1 which is 5-O-(4-methylbenzyl)-1,2:3,4-bis-O-isopropylidene-xylite.

15. Compound according to claim 1 which is 5-O-(3,4-dimethylbenzyl)-1,2:3,4-bis-O-isopropylidene-xylite.

16. Compound according to claim 1 which is 5-O-(2-fluorobenzyl)-1,2:3,4-bis-O-isopropylidene-xylite.

17. Compound according to claim 1 which is 5-O-(3-fluorobenzyl)-1,2:3,4-bis-O-isopropylidene-xylite.

18. Compound according to claim 1 which is 5-O-(4-fluorobenzyl)-1,2:3,4-bis-O-isopropylidene-xylite.

19. Compound according to claim 1 which is 5-O-(3-trifluoromethylbenzyl)-1,2:3,4-bis-O-isopropylidene-xylite.

20. Compound according to claim 1 which is 5-O-benzyl-1,2:3,4-bis-O-isopropylidene-xylite.

21. Compound according to claim 1 which is 5-O-(2,4-dichlorobenzyl)-1,2:3,4-bis-O-(diethyl-methylene)-xylite.

22. Compound according to claim 1 which is 5-O-(2,6-dichlorobenzyl)-1,2:3,4-bis-O-(ethyl-methyl-methylene)-xylite.

23. Compound according to claim 1 which is 5-O-(2,4-dichlorobenzyl)-1,2:3,4-bis-O-(ethyl-methyl-methylene)-xylite.

24. Compound according to claim 1 which is 5-O-(2-chlorobenzyl)-1,2:3,4-bis-O-(ethyl-methyl-methylene)-xylite.

25. Compound according to claim 1 which is 5-O-(2-methylbenzyl)-1,2:3,4-bis-O-(ethyl-methyl-methylene)-xylite.

26. Compound according to claim 1 which is 5-O-(2,6-dichlorobenzyl)-1,2:3,4-bis-O-(methyl-propyl-methylene)-xylite.

27. Compound according to claim 1 which is 5-O-(2,4-dichlorobenzyl)-1,2:3,4-bis-O-(methyl-propyl-methylene)-xylite.

28. Compound according to claim 1 which is 5-O-(2-methylbenzyl)-1,2:3,4-bis-O-(methyl-propyl-methylene)-xylite.

29. Compound according to claim 1 which is 5-O-(2-chlorobenzyl)-1,2:3,4-bis-O-(methyl-propyl-methylene)-xylite.

30. Compound according to claim 1 which is 5-O-(2,6-dichlorobenzyl)-1,2:3,4-bis-O-(diethyl-methylene)-xylite.

31. Compound according to claim 1 which is 5-O-(2-methylbenzyl)-1,2:3,4-bis-O-(diethyl-methylene)-xylite.

32. Compound according to claim 1 which is 5-O-(2-chlorobenzyl)-1,2:3,4-bis-O-(diethyl-methylene)-xylite.

33. Compound according to claim 1 which is 5-O-(2-methylbenzyl)-1,2:3,4-bis-O-(benzyl-methyl-methylene)-xylite.

34. Compound according to claim 1 which is 5-O-(2-chlorobenzyl)-1,2:3,4-bis-O-(benzyl-methyl-methylene)-xylite.

35. Compound according to claim 1 which is 5-O-(2,4-dichlorobenzyl)-1,2:3,4-bis-O-(benzyl-methyl-methylene)-xylite.

36. Compound according to claim 1 which is 5-O-(2,6-dichlorobenzyl)-1,2:3,4-bis-O-(benzyl-methyl-methylene)-xylite.

37. Compound according to claim 1 which is 5-O-(2-methylbenzyl)-1,2:3,4-bis-O-(benzyl-methyl-methylene)-xylite.

38. Compound according to claim 1 which is 5-O-(2-chlorobenzyl)-1,2:3,4-bis-O-(1,1-tetramethylene-methylene)-xylite.

39. Compound according to claim 1 which is 5-O-(2,4-dichlorobenzyl)-1,2:3,4-bis-O-(1,1-tetramethylene-methylene)-xylite.

40. Compound according to claim 1 which is 5-O-(2-chlorobenzyl)-1,2:3,4-bis-O-(butyl-methyl-methylene)-xylite.

41. Compound according to claim 1 which is 5-O-(2,4-dichlorobenzyl)-1,2:3,4-bis-O-(butyl-methyl-methylene)-xylite.

42. Compound according to claim 1 which is 5-O-(2-methylbenzyl)-1,2:3,4-bis-O-(1,1-tetramethylene-methylene)-xylite.

43. Compound according to claim 1 which is 5-O-(2,6-dichlorobenzyl)-1,2:3,4-bis-O-(butyl-methyl-methylene)-xylite.

44. Compound according to claim 1 which is 5-O-(2,6-dichlorobenzyl)-1,2:3,4-bis-O-(1,1-tetramethylene-methylene)-xylite.

45. Compound according to claim 1 which is 5-O-(2-chlorobenzyl)-1,2:3,4-bis-O-[(2-phenylethyl)-methyl-methylene]-xylite.

46. Compound according to claim 1 which is 5-O-(2,4-dichlorobenzyl)-1,2:3,4-bis-O-[(2-phenylethyl)-methyl-methylene]-xylite.

47. Compound according to claim 1 which is 5-O-(2,4-dichlorobenzyl)-1,2:3,4-bis-O-(methyl-methylene)-xylite.

48. Compound according to claim 1 which is 5-O-(4-phenylbenzyl)-1,2:3,4-bis-O-isopropylidene-xylite.

49. Compound according to claim 1 which is 5-O-(4-cyanbenzyl)-1,2:3,4-bis-O-isopropylidene-xylite.

50. Compound according to claim 1 which is 5-O-(2,6-dichlorobenzyl)-1,2:3,4-bis-O-(2-phenylethyl)-methyl-methylene-xylite.

51. Compound according to claim 1 which is 5-O-(2-methylbenzyl)-1,2:3,4-bis-O-(2-phenylethyl)-methyl-methylene-xylite.

52. Compound according to claim 1 which is 5-O-(2,6-dichlorobenzyl)-1,2:3,4-bis-O-(4-chlorophenyl-methylene)-xylite.

53. Compound according to claim 1 which is 5-O-(2-chlorobenzyl)-1,2:3,4-bis-O-(phenylmethylene)-xylite.

54. Compound according to claim 1 which is 5-O-(2,4-dichlorobenzyl)-1,2:3,4-bis-O-(4-chlorophenyl-methylene)-xylite.

55. Compound according to claim 1 which is 5-O-(2-methylbenzyl)-1,2:3,4-bis-O-(4-chlorophenyl-methylene)-xylite.

56. Compound according to claim 1 which is 5-O-(2,6-dichlorobenzyl)-1,2:3,4-bis-O-(phenyl-methylene)-xylite.

57. Compound according to claim 1 which is 5-O-(2,6-dichlorobenzyl)-1,2:3,4-bis-O-(methyl-methylene)-xylite.

58. Compound according to claim 1 which is 5-O-(2-methylbenzyl)-1,2:3,4-bis-O-(methyl-methylene)-xylite.

59. Compound according to claim 1 which is 5-O-(2-chlorobenzyl)-1,2:3,4-bis-O-(methyl-methylene)-xylite.

60. Compound according to claim 1 which is 5-O-(2,6-dichlorobenzyl)-1,2:3,4-bis-O-(chloromethyl-methylene)-xylite.

61. Compound according to claim 1 which is 5-O-(2,4-dichlorobenzyl)-1,2:3,4-bis-O-(chloromethyl-methylene)-xylite.

62. Compound according to claim 1 which is 5-O-(2-methylbenzyl)-1,2:3,4-bis-O-(chloromethyl-methylene)-xylite.

63. Compound according to claim 1 which is 5-O-(2-chlorobenzyl)-1,2:3,4-bis-O-(chloromethyl-methylene)-xylite.

64. Compound according to claim 1 which is 5-O-(2,6-dichlorobenzyl)-1,2:3,4-bis-O-(methylene)-xylite.

65. Compound according to claim 1 which is 5-O-(2,4-dichlorobenzyl)-1,2:3,4-bis-O-(methylene)-xylite.

66. Compound according to claim 1 which is 5-O-(2-methylbenzyl)-1,2:3,4-bis-O-(methylene)-xylite.

67. Compound according to claim 1 which is 5-O-(2,4-dichlorobenzyl)-1,2:3,4-bis-O-(methyl-octyl-methylene)-xylite.

68. Compound according to claim 1 which is 5-O-(2,6-dichlorobenzyl)-1,2:3,4-bis-O-(methyl-octyl-methylene)-xylite.

69. Compound according to claim 1 which is 5-O-(2-methylbenzyl)-1,2:3,4-bis-O-(methyl-octyl-methylene)-xylite.

70. Compound according to claim 1 which is 5-O-(2-chlorobenzyl)-1,2:3,4-bis-O-(methyl-octyl-methylene)-xylite.

71. Compound according to claim 1 which is 5-O-(2,4-dichlorobenzyl)-1,2:3,4-bis-O-(phenyl-methylene)-xylite.

72. Compound according to claim 1 which is 5-O-(2-methylbenzyl)-1,2:3,4-bis-O-(phenyl-methylene)-xylite.

73. Compound according to claim 1 which is 5-O-(2,4-dichlorobenzyl)-1,2:3,4-bis-O-[(2,6-dichlorophenyl)-methylene]-xylite.

74. Compound according to claim 1 which is 5-O-(2-methylbenzyl)-1,2:3,4-bis-O-[(2,6-dichlorophenyl)-methylene]-xylite.

75. Compound according to claim 1 which is 5-O-(2-chlorobenzyl)-1,2:3,4-bis-O-(2,6-dichlorophenyl)-methylene-xylite.

76. Compound according to claim 1 which is 5-O-(2,6-dichlorobenzyl)-1,2:3,4-bis-O-[(2,6-dichlorophenyl)-methylene]-xylite.

77. Compound according to claim 1 which is 5-O-(2,4,6-tribromobenzyl)-1,2:3,4-bis-O-isopropylidene-xylite.

78. Compound according to claim 1 which is 5-O-(1-phenylethyl)-1,2:3,4-bis-O-isopropylidene-xylite.

79. Compound according to claim 1 which is 5-O-[1-(2,4-dichlorophenyl)-ethyl]-1,2:3,4-bis-O-isopropylidene-xylite.

80. Compound according to claim 1 which is 5-O-[1-(2,6-dichlorophenyl)-ethyl]-1,2:3,4-bis-O-isopropylidene-xylite.

81. Compound according to claim 1 which is 5-O-(2,6-dichlorobenzyl)-1,2:3,4-bis-O-(methyl-phenoxymethyl-methylene)-xylite.

82. Compound according to claim 1 which is 5-O-(2,4-dichlorobenzyl)-1,2:3,4-bis-O-(methyl-phenoxymethyl-methylene)-xylite.

83. Composition having growth regulatory activity for plants, having at least one plant-growth regulating amount of a compound according to claim 1 in mixture with carrier material and/or adjuvants.

84. Method of influencing the vegetative and generative growth of legumes, comprising applying a growth-influencing amount of the composition according to claim 83.

85. Method according to claim 84, for use with soy.

* * * * *